United States Patent
Kim et al.

(10) Patent No.: US 10,613,068 B2
(45) Date of Patent: Apr. 7, 2020

(54) COLORIMETRIC SENSOR MATERIAL FOR DETECTING HYDROGEN SULFIDE GAS, WHICH INCLUDES ONE-DIMENSIONAL POLYMER NANOFIBER COUPLED TO LEAD ACETATE PARTICLES OBTAINED BY HIGH TEMPERATURE STIRRING AND QUENCHING, AND METHOD OF THE SAME

(71) Applicant: Korea Advanced Institute of Science and Technology, Daejeon (KR)

(72) Inventors: Il-Doo Kim, Daejeon (KR); Jun Hwe Cha, Daejeon (KR); Won-Tae Koo, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 346 days.

(21) Appl. No.: 15/454,954

(22) Filed: Mar. 9, 2017

(65) Prior Publication Data
US 2017/0261479 A1 Sep. 14, 2017

(30) Foreign Application Priority Data
Mar. 11, 2016 (KR) .................. 10-2016-0029435

(51) Int. Cl.
| | | |
|---|---|---|
| *G01N 33/00* | (2006.01) | |
| *D01D 5/00* | (2006.01) | |
| *D01F 1/06* | (2006.01) | |
| *D01F 6/54* | (2006.01) | |
| *G01N 21/78* | (2006.01) | |
| *G01N 21/75* | (2006.01) | |

(52) U.S. Cl.
CPC ........ *G01N 33/0044* (2013.01); *D01D 5/003* (2013.01); *D01F 1/06* (2013.01); *D01F 6/54* (2013.01); *G01N 21/783* (2013.01); *D10B 2321/10* (2013.01); *G01N 2021/757* (2013.01); *Y02A 50/25* (2018.01)

(58) Field of Classification Search
CPC ............ G01N 33/0044; G01N 21/783; G01N 2021/757; D01F 1/06; D01F 6/54; D01D 5/003; D10B 2321/10; Y02A 50/25
See application file for complete search history.

(56) References Cited

U.S. PATENT DOCUMENTS 4,174,202 A * 11/1979 Simpson ................ G01N 31/02
422/403

FOREIGN PATENT DOCUMENTS

| JP | 2005-037188 A | 2/2005 |
| JP | 2008-216147 A | 9/2008 |
| KR | 10-0851431 B1 | 8/2008 |
| KR | 100851431 B1 * | 8/2008 |
| KR | 10-1203761 B1 | 11/2012 |

(Continued)

OTHER PUBLICATIONS

Yao et al.,"High Strength and High Modulus Electrospun Nanofibers" Fibers 2014, 2, 158-187 (Year: 2014).*

*Primary Examiner* — Dennis White
(74) *Attorney, Agent, or Firm* — Masuvalley & Partners (57) ABSTRACT

Disclosed are polymer nanofiber sensors for detecting gas, which generates visible color change although a specific gas having a concentration of less than 1 ppm is exposed to the sensor in a short time, in which it is impossible to detect the gas using existing colorimetric sensors, through securing high surface area and porosity, and a method of the same.

8 Claims, 8 Drawing Sheets

(56) References Cited

FOREIGN PATENT DOCUMENTS

KR            101203761 B1 * 11/2012
KR    10-2014-0018752      2/2014

* cited by examiner

COLORIMETRIC SENSOR MATERIAL FOR DETECTING HYDROGEN SULFIDE GAS, WHICH INCLUDES ONE-DIMENSIONAL POLYMER NANOFIBER COUPLED TO LEAD ACETATE PARTICLES OBTAINED BY HIGH TEMPERATURE STIRRING AND QUENCHING, AND METHOD OF THE SAME

CROSS-REFERENCE TO RELATED APPLICATIONS

A claim for priority under 35 U.S.C. § 119 is made to Korean Patent Application No. 10-2016-0029435 filed Mar. 11, 2016, in the Korean Intellectual Property Office, the entire contents of which are hereby incorporated by reference.

BACKGROUND

The present disclosure relates to a colorimetric sensor material in which one-dimensional polymer nanofiber is coupled to fine dye particles generating color change when the dye particles are exposed to a specific gas, a gas sensor, and a method of the same. More particularly, in a method of manufacturing an electrospinning solution, after a dye is stirred at a high temperature of more than melting point to be liquefied, the liquefied dye may be quenched to control crystal growth which is generated in a dry process at room temperature, and dye particles for detecting hydrogen sulfide gas may be formed in which the dye particles finely dispersed by a polymer dissolved in a solvent, without a mass. A polymer nanofiber sensor for detecting hydrogen sulfide having high porosity and a high surface area, in which an electrospinning solution dispersed fine lead acetate particles performs an electrospinning process such that the fine dye particles are coupled to an inner part and a surface of an one-dimensional polymer fiber while each having a biconvex lens shape, in which a ratio of a long axis to a short axis is more than 1, and a method of manufacturing the same may be provided.

Various noxious gases are used across industrial technology. A gas sensor having a high sensitivity and fast response are necessary to monitor a noxious gas leak generated at a work area for preventing a severe accident or damage for humans. In additional, a gas sensor may be used for measurement of a degree of air pollution and measurement of air quality of a room as air pollution becomes serious due to industrialization.

In recent, an exhalation sensor for health care capable of easily diagnosing a specific disease by detecting a biomarker gas in exhalation of respiration is studied. Various biomarker gases such as hydrogen sulfide, pentane, toluene, acetone, nitrogen monoxide, and ammonia are generated by reaction of cells of a human body through respiration and are discharged through respiration. It is reported that these gases function as biomarkers for halitosis, cardiac disease, a lung cancer, diabetes, and kidney disease. Since hundreds of various gases are blended in exhalation, a specific biomarker should be selectively detected. Furthermore, since the biomarker gas of exhalation is discharged at a low concentration having a range of 10 part per billion (ppb) to 10 part per million (ppm), a gas sensor having high sensitivity for precisely detecting the gas having a concentration of 10 ppb should be developed.

The gas sensor may be mainly classified into a gas chromatography, a variable resistance gas sensor, and a colorimetric gas sensor based on a gas detection operation manner. In the gas chromatography, a specimen is injected into an inlet such that evaporation occurs and the evaporated material is separated by columns of the gas chromatography. Compound components of the separated gas phase are displayed at a monitor using an electric signal proportional to the amount of the detected gas through a detector. The gas chromatography performs a precisely quantitative analysis but is expensive and has a large size such that it is improper to be portable. Furthermore, the variable resistance gas sensor based on a metal oxide semiconductor detects a specific gas, in which adsorption-desorption of the specific gas on the metal oxide semiconductor generates variable resistance such that the specific gas is detected. The variable resistance gas sensor has simple sensor system constitutions and is easy to carry but has low sensitivity and selectivity, in comparison with the gas chromatography. Meanwhile, the colorimetric sensor capable of visually detecting color change when being exposed to the specific gas is studied. In the colorimetric sensor, when a material used as a dye reacts with a specific gas, the reaction influences a band structure of the material such that an absorption wavelength of a visible light is changed while color change occurs. In addition, an analyte gas may be detected through a colored product generated by reaction of the analyte gas and the dye. Moreover, the colorimetric sensor does not need additional circuit designing and measuring equipment and has a test paper shape, thereby being portable. However, gas sensitivity and selectivity are less than the gas chromatography and the variable resistance gas sensor.

Various nanostructures are developed for development of a colorimetric sensor having high sensitivity. Since a detecting material based on a nanostructure such as a nanoparticle, a nanofiber, a nanotube, and a nano-hollow structure has a large area in comparison to an existing material such as a thick film, superior gas detecting properties may be provided. Particularly, since the colorimetric sensor generates color change by a surface reaction of the dye material and the analyte gas, reacting sites, in which gas particles are in contact with the dye material, are increased by application of the nanostructures such that gas sensitivity can be improved. lead(II) acetate ($Pb(CH_3COO)_2$)) includes an anhydrous state and a trihydrate state in natural. lead(II) acetate anhydrous has the melting point of 280° C. and lead(II) acetate trihydrate has the melting point of 75° C. The above two states of lead acetate have already been used as a dye capable of selectively detecting hydrogen sulfide in a film type in an industrial field to monitor leak of hydrogen sulfide. The colorimetric sensor is used when lead(II) acetate reacts with the hydrogen sulfide ($H_2S$) to form brown lead sulfide (PbS). However, there is a detection limit of 5 ppm such that hydrogen sulfide gas of less than 1 ppm is not detected. Hydrogen sulfide, i.e. a biomarker of a halitosis patient, has a concentration range of 50 ppb to 80 ppb in exhalation of a normal human but hydrogen sulfide has 1 ppm to 2 ppm in exhalation of a halitosis patient. However, since a teat paper for detecting hydrogen sulfide in market has poor sensitivity, it is impossible to diagnose halitosis due to low concentration of hydrogen sulfide.

Accordingly, it is necessary to develop a colorimetric sensor material having a large surface area for providing a maximum reaction area capable of being in contact with an analyte gas. In the case of a colorimetric sensor having a thick film type, gas molecules are not diffused into a detecting material due to absence of pores such that reaction is limited to a surface of the detecting material. For improvement of gas sensitivity, a colorimetric sensor in a porous structure is developed such that the gas molecules can react with the dye in an inner part as well as the surface reaction. Particularly, in the case of lead(II) acetate, after lead(II) acetate is dissolved, recrystallization growth occurs to have a size between several micrometers and tens-of-micrometer such that it is important to secure process technology in which there is fine crystal distribution in recrystallization growth for obtaining a high specific surface area.

SUMMARY

Embodiments of the inventive concept provide a method of manufacturing a polymer nanofiber sensor for detecting hydrogen sulfide gas, in which it is easy to synthesize a nanostructure, which maximally provides a reaction area for contact between a dye generating color change of a specific gas and the specific gas.

Embodiments of the inventive concept provide a method of manufacturing fine dye particles, in which a dye is stirred at a high temperature of more than melting point to be liquefied in a manufacturing process of an electrospinning solution, and then is quenched to control crystal growth generated in a dry process at a room temperature, and a polymer dissolved in a solvent of the electrospinning solution prevents dye particles from clumping.

Embodiments of the inventive concept provide a method of manufacturing colorimetric sensor for detecting hydrogen sulfide having a membrane shape using an electrospinning process, in which the fine dye particles are uniformly coupled to one-dimensional polymer nanofiber, after a small quantity of dye material and the polymer are blended to manufacture an electrospinning solution.

Embodiments of the inventive concept provide a method of uniformly coupling fine lead(II) acetate dye particles to an inner part and a surface of a polymer/dye complex nanofiber, which is synthesized using an electrospinning process. Therefore, a polymer nanofiber sensor for detecting hydrogen sulfide, which is coupled to fine lead(II) acetate particles capable of detecting an a small quantity of analyte gas using large surface area and high porosity of the polymer/dye complex nanofiber.

According to an aspect of an embodiment, lead(II) acetate trihydrate has a low melting point such that after a dye is stirred in a solution in which a polymer is dissolved at a high temperature, a solution in which fine dye particles are dispersed, and which is formed through a quenching, may be provided. Herein, in order that fine dye particles are uniformly coupled to an one-dimensional nanofiber dye/polymer complex is synthesized, the dye particles are uniformly coupled to an inner part of an outer part of the nanofiber using an electrospinning process and each particle which is elongated in a longitudinal direction in the electrospinning process to have a biconvex lens shape in which a ratio a long axis to a short axis is more than 1 is formed on the nanofiber, such that a polymer nanofiber sensor material for detecting hydrogen sulfide coupled to fine lead acetate particles having large surface area and high porosity and a method of manufacturing the same may be provided.

According to an aspect of an embodiment, a method of manufacturing a colorimetric sensor material includes (a) forming an electrospinning solution in which lead(II) acetate trihydrate and a polymer is blended in a solvent, lead(II) acetate trihydrate and the polymer blended in the solvent is stirred at a high temperature to liquefy lead(II) acetate trihydrate, (b) forming crystals of lead(II) acetate trihydrate liquefied in the electrospinning solution through quenching, (c) forming nanofibers in which the dye is coupled to the polymer to form a nanofiber complex and lead(II) acetate trihydrate uniformly remains on an inner part and an surface of the nanofiber using an elecrospinning process of the quenched electrospinning solution, and (d) forming a complex nanofiber membrane in which the complex nanofiber formed by the electrospinning process is directly discharged on nonwoven fabrics.

In step (a), lead(II) acetate trihydrate may be used as the dye material. Since lead(II) acetate anhydrous has the melting point of 280° C., introduction of lead(II) acetate anhydrous may melt and decompose polymer blended therein when a temperature of lead(II) acetate anhydrous is increased to the melting point in the electrospinning process. However, since the melting point of lead(II) acetate trihydrate is 75° C. which is lower than glass transition points of most of polymers, the other polymers blended in lead(II) acetate trihydrate may be stable when stirring at liquefaction point. Accordingly, step (a) may be a process in which lead(II) acetate trihydrate and the polymer are blended such that the electrospinning solution may be formed by stirring at a high temperature of more than the melting point of the dye, which does not influence the polymer.

The polymer may include one selected from polymethyl methacrylate (PMMA), polyacryl copolymer, polyvinyl acetate copolymer, polymethyl alcohol (PVA), polymethyl acrylate (PMA), polyvinyl acetate (PVAc), polyperfuryl alcohol (PPFA), polystyrene (PS), polyvinylpyrrolidone (PVP), polystylene copolymer, polyethylene oxide (PEO), polyurethane, polyurethane copolymer, cellulose acetate, polypropylene oxide (PPO), polyacrylonitrile (PAN), polycarbonate (PC), polyvinyl chloride (PVC), polymer carprolactone (PCL), polyvinyl fluoride, polyaniline (PANI), styrene-acrylonitrile (SAN), polyvinyl alcohol (PVA), polycarbonate (PC), polymer(vinylidene fluoride) (PVDF), polymer(vinylidene fluoride) copolymer, polyimide, polyethylene (PE), polyethylene terephthalate (PET), polypropylene (PP), cellulose, acetate butyrate, and a cellulose derivative. When the electrospinning solution is formed, the dye material may have a weight rate range of 0.5 to 90 wt % with respect to polymer included in the polymer nanofiber.

The solvent may include one of dimethylformamide (DMF), ethanol, acetone, dimethylacetamide (DMAc), tetrahydrofuran, toluene, dimethyl sulfoxide (DMSO), and ethylene glycol (EG) or a combination of at least two thereof. A weight percent of the solvent of the dye may include a range of 50 wt % to 99 wt % with respect to lead(II) acetate trihydrate constituting the dye/polymer nanofiber complex.

Step (b) may be a process in which the electrospinnig solution is stirred at a high temperature of or above the melting point in step (a). When lead(II) acetate trihydrate is bought in market, an average size may be 200 μm. However, when each dye particle has a size of less than 1 μm, the dye particles may be coupled to the nanofiber through the electrospinning process. Since, in general, the polymer nanofiber obtained through electrospinning process has a size range of 100 nm to 1 μm, the dye particles may have the same size range as the nanofiber or less than the nanofiber. Accordingly, in order that the dye particles having the similar size to the nanofiber are obtained, the electrospinning solution obtained through high-temperature stirring of step (a) may be quenched at a temperature of less than 25° C. such that crystal growth generated in room-temperature dry process may be controlled. The fine dye particles may be synthesized by the polymer dissolved in the solvent without bulk. The dye particles may be coupled to an outer part and an inner part of the fiber in the electrospinning process. The fine dye particles formed by high-temperature stirring and quenching may have an average diameter range of 50 nm to 2 μm. A beaker including the electrospinning solution at a higher temperature than the melting point of lead(II) acetate trihydrate, may be dipped into a cooling water such that the polymer solution may be formed in which each fine dye particle having a size of less than 1 μm are dispersed.

In step (c), the electrospinning solution including the fine dye particles formed in step (b) may be synthesized to the dye/polymer complex nanofiber using an electrospinning equipment. The fine dye particles may remain at the inner and outer parts of the nanofiber having high porosity and large surface area. Furthermore, in the electrospinning process, the polymer may be elongated in a longitudinal direction while the fine dye particles may remain on the polymer and may be discontinuously formed in the shape of a biconvex lens in which a ratio of a long axis to a short axis of each particle was more than 1. The dye particles should be intensively coupled to inner and outer parts of a matrix of the polymer nanofiber because the dye particles may be detached from the polymer nanofiber before measurement when dye coupling strength is weak. When the electrospinning process is used, the fine dye particles may be dispersed in the polymer while the dye/polymer complex fibers are being obtained, such that the dye coupling strength is strong enough. When the crystal particles are large, the particles may be detached from the nanofiber and reaction sites may be decreased, such that color change may be not distinguished with the naked eye. Accordingly, the dye particles may be intensively coupled to the nanofiber without detachment and lead(II) acetate having small sizes may be uniformly coupled to the nanofiber, thereby improving colorimetric efficiency.

In step (d), the dye/polymer complex nanofiber membrane may be formed and collected on a collector by the electrospinning process. The dye/polymer complex nanofiber may include a size range of 50 nm to 10 μm. In the dye/polymer complex nanofiber to which the lead(II) acetate trihydrate is coupled, the dye particles remaining on the polymer nanofiber may react with hydrogen sulfide ($H_2S$) when being exposed to the gas such that PbS may be deposited and a color may be changed. Under a dry condition, it turns brown. Otherwise, under a high humidity condition, color transition into brown may occur. The polymer nanofiber may include a diameter range of 100 nm to 1000 nm. As the diameter of the nanofiber is decreased, a specific area may increase such that reaction sites between the gas and the dye particles which are exposed on the surface of the nanofiber may be increased. Therefore, the nanofiber may have an average diameter of about 300 nm.

The dye/polymer complex nanofiber membrane obtained on the collector may include a thickness range of 5 μm to 100 μm.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Embodiments of the present disclosure relates to a method of manufacturing a polymer nanofiber sensor for detecting hydrogen sulfide gas in which, after a dye is stirred at a higher temperature than the melting point to be liquefied during manufacturing an electrospinning solution, fine dye particles are uniformly dispersed in a polymer solution through a quenching process and the dye particles are coupled to an inner part and a surface of the polymer nanofiber without desorption using an electrospinning process.

As an embodiment, a dye/polymer complex colorimetric nanofiber sensor, in which lead(II) acetate trihydrate, i.e. a dye material for generating color change when being exposed to hydrogen sulfide gas, uniformly remains on an inner part and an outer part (a surface) of an one-dimensional polymer nanofiber, and a method of manufacturing the same are provided.

In a detailed embodiment, among lead(II) acetate anhydrous ($Pb(CH_3COO)_2$, 280° C. of the melting point) and lead(II) acetate trihydrate ($Pb(CH_3COO)_2.3H_2O$, 75° C. of the melting point), when lead(II) acetate anhydrous having high melting point is used in a manufacturing process of an electrospinning solution, such a high temperature of the melting point of lead(II) acetate anhydrous may melt and decompose polymers blended therein. Accordingly, lead(II) acetate trihydrate having a relatively low melting point may be used as dye particles such that lead(II) acetate trihydrate may be stirred at a higher temperature than the melting point to be liquefied. Then, the dye particles are recrystallized through a quenching process to have fine sizes and the dye particles of tens-of-nanometer to hundreds-of-nanometer are coupled to the polymer nanofibers obtained through the electrospinning. In this process, each particle is formed in the shape of a biconvex lens shape in which a ratio of a long axis to a short axis of each particle is more than 1 such that a nanofiber colorimetric sensor membrane including the particles may be provided. Since the dye particles are strongly coupled to the inner part and the surface of each nanofiber constituting an one-dimensional porous fiber structure, an analyte gas may be diffused into a three-dimensional structure including the dye particles such that reaction sites confined to the surface are provided to the inner part, thereby significantly increasing reaction area.

In embodiments of the present disclosure, the polymer nanofiber sensor to which the dye is coupled may be massively manufactured using the electrospinning process. A polymer nanofiber sensor for detecting a gas in which, since the polymer nanofiber sensor for detecting the gas secures a surface area and porosity higher than an existing test paper for detecting hydrogen sulfide, visible color change to a specific gas having a low concentration of less than 1 ppm, which is impossible to be detected using existing colorimetric sensors, occurs, and a method of the same may be provided.

Hereinafter, in example 1 which will be described, a manufacturing process of a polymer nanofiber sensor for detecting hydrogen sulfide gas used as a specific gas is described in detail. Furthermore, in comparative example 1, dye particles bought in market was used as a material for a colorimetric sensor of hydrogen sulfide gas. In comparative example 2, a polymer nanofiber sensor for detecting hydrogen sulfide was manufactured using an electrospinning solution which did not perform high-temperature stirring and quenching. Colorimetric variation of example 1, comparative example 1, and comparative example 2 upon exposure of a small quantity of hydrogen sulfide gas were compared. Herein, examples 1 may show improved colorimetric properties in comparison to comparative example 1 and comparative example 2 since reaction sites and porosity are increased due to increase of a specific surface area.

Figure 1:
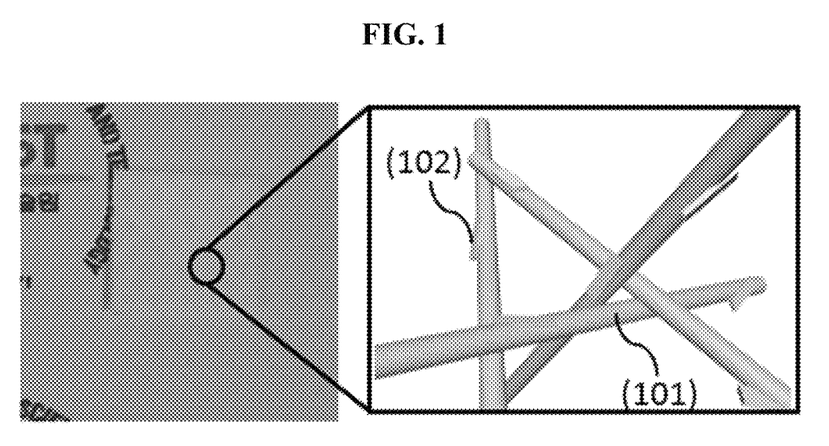
FIG. 1 is a block diagram of a dye/polymer complex nanofiber colorimetric sensor in which nanoparticles are uniformly coupled on an inner part and a surface of the nanofiber according to an embodiment of the present disclosure.

FIG. 1 is a block diagram of a colorimetric sensor for detecting hydrogen sulfide gas, in which fine dye particles are coupled to an inner part and a surface of a polymer nanofiber. The polymer nanofiber 101 illustrated in FIG. 1 may include a diameter range of 50 nm to 10 μm. The diameter of the polymer nanofiber 101 may be adjusted by discharge speed, a diameter of a nozzle, viscosity of a spinning solution, or an applied voltage. When the diameter of the nanofiber is increased, the dye particles are formed on the inner part of the fiber instead of the surface of the fiber, such that the dye particles are not reacted to a gas, which is supposed to be detected, thereby decreasing detectability. Whereas, when the nanofiber is thin, the size of each dye particle is relatively increased such that the dye particles are not coupled to the fiber, such that the particles may be dispersed between nanofibers. Accordingly, it is effective that the diameter of the nanofiber 101 which functions as a supporter of the dye/polymer complex nanofiber may be 50 nm to 10 μm. The sensor, which is structurally stable and has the most noticeable color change to the analyte, may be advantageously manufactured using the polymer nanofiber 101 having the diameter range of 100 nm to 1000 nm.

Furthermore, the size of each dye particle 102 coupled to the polymer nanofiber 101 is an important component influencing colorimetric sensitivity. The size (one of a diameter, a length, and a thickness based on a shape of the dye particle) of the dye particle may include a range of 10 nm to 2 μm. As the size of the dye particle is decreased, the dye particles provide high surface area. However, when the size of the dye particle is much less than the diameter of the nanofiber, in the electrospinning process, the dye particles remain in the inner part of the nanofiber such that the dye particles are not reacted to the detecting gas, such that preventing the dye particles from functioning as the reaction site. In contrast with, when the dye particle is too large, in the electrospinning process, the surface area thereof is greatly decreased and the dye particles are not coupled to the polymer nanofiber such that the dye particles each of which maintains an original shape are dispersed in the fibers. When the particles are disposed in pores of the polymer nanofiber, the particles prevent diffusion of the detecting gas and prevent colorimetric reaction of the dye coupled to the nanofiber disposed in a deep-set region. Accordingly, the dye particle may include the size range of 10 nm and 2 μm.

In addition, when the ratio of the long axis to the short axis of each dye particle 102 coupled to the polymer nanofiber 101 is more than 1 to have the biconvex lens shape, a diameter of the short axis of the dye particle may include a range of 10 to 500 nm and a diameter of the long axis may include a range of 100 nm to 5 μm.

Figure 2:
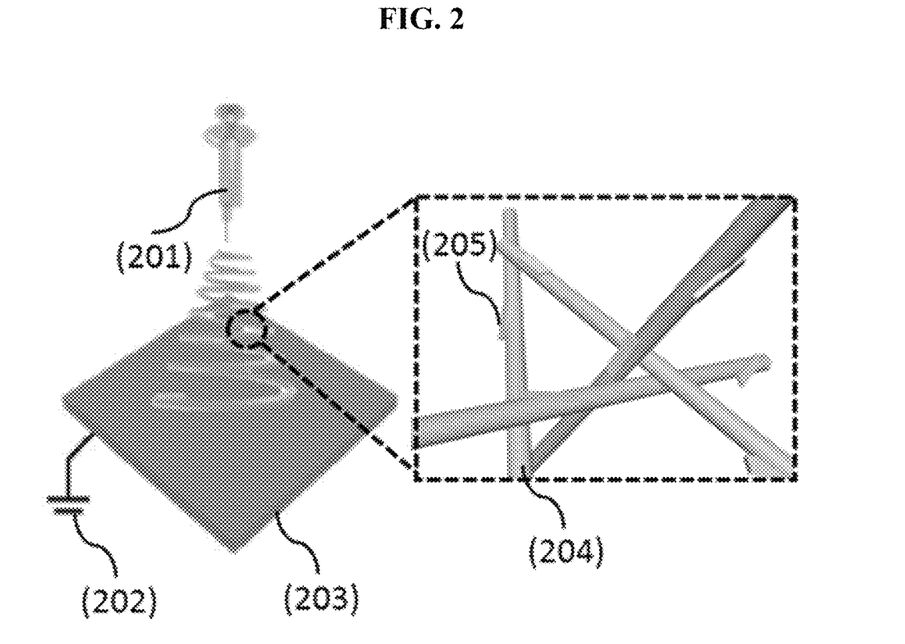
FIG. 2 is a block diagram of a dye/polymer complex nanofiber colorimetric sensor in which nanoparticles are uniformly coupled on an inner part and a surface of the nanofiber using an electrospinning process according to an embodiment of the present disclosure.

FIG. 2 is a block diagram of an electrospinning equipment used in a first embodiment of the present disclosure. Hereinafter, the electrospinning process will be described. Strong electric field is applied to a nozzle 201 disposed at the end of an injector using a high voltage application device 202 such that a solvent of the electrospinning solution discharged from the nozzle 201 is vaporized and the dye/polymer complex nanofiber is formed and collected on a collector 203. The complex fiber discharged from the nozzle is an one-dimensional nanofiber. any solvent is used to manufacture the electrospinning solution as long as the solvent dose not dissolve the dye, i.e. lead(II) acetate trihydrate. For example, the solvent may include one of dimethylformamide (DMF), ethanol, acetone, dimethylacetamide (DMAc), tetrahydrofuran, toluene, dimethyl sulfoxide (DMSO), and ethylene glycol (EG), or a combination of at least two thereof.

The dye/polymer complex colorimetric nanofiber includes polymer nanofibers 204 maintaining a fiber structure and dye particles 206 which are uniformly coupled to the polymer nanofibers 204 and are reacted to an detecting gas such that color change occurs. The polymer may include one selected from polymethyl methacrylate (PMMA), polyacryl copolymer, polyvinyl acetate copolymer, polymethyl alcohol (PVA), polymethyl acrylate (PMA), polyvinyl acetate (PVAc), polyperfuryl alcohol (PPFA), polystyrene (PS), polyvinylpyrrolidone (PVP), polystylene copolymer, polyethylene oxide (PEO), polyurethane, polyurethane copolymer, cellulose acetate, polypropylene oxide (PPO), polyacrylonitrile (PAN), polycarbonate (PC), polyvinyl chloride (PVC), polymer carprolactone (PCL), polyvinyl fluoride, polyaniline (PANI), styrene-acrylonitrile (SAN), polyvinyl alcohol (PVA), polycarbonate (PC), polymer(vinylidene fluoride) (PVDF), polymer(vinylidene fluoride) copolymer, polyimide, polyethylene (PE), polyethylene terephthalate (PET), polypropylene (PP), cellulose, acetate butyrate, and a cellulose derivative, or a combination of at least two thereof. A content of the polymer to the solvent is not limited. However, in general, the solvent may be selected from a range of 5 wt % to 30 wt % with respect to the solvent for having proper viscosity to perform the electrospinning process.

The electrospinning solution injected to the nozzle includes the dye 205, which is reacted to hydrogen sulfide such that the dye 205 turns brown. In the above-described process, lead(II) acetate trihydrate having a relatively low melting point may be used as a material constituting the dye 205. Lead acetate is in an anhydrous state and a trihydrate state in nature. In the case of lead(II) acetate anhydrous, it is reported that its melting point is 280° C., and when a temperature of lead(II) acetate anhydrous is increased to liquefaction point, other polymers in the solution does not maintain original shapes or properties thereof since the other polymers are melted or to be decomposed. However, since the melting point of lead(II) acetate trihydrate is 75° C. which is lower than glass transition point of most of polymers, polymers blended in lead(II) acetate trihydrate may maintain original states thereof, such that polymers are not affected from the temperature although lead(II) acetate trihydrate is stirred at the liquefaction point thereof. Therefore, lead(II) acetate trihydrate may be selected as the material constituting the dye 205. A weight percent of the solvent of the dye 205 may include a range of 50 wt % to 99 wt % with respect to lead(II) acetate trihydrate constituting the dye/polymer nanofiber complex. A rate of the spinning solution discharged from the nozzle may be selected from a range of 0.1 μL/min to 250 μL/min based on viscosity of the spinning solution. A voltage applied to the nozzle may be selected between 5 kV to 30 kV. A distance between the nozzle and the collector may be selected from a range of 3 cm to 50 cm.

Figure 3:
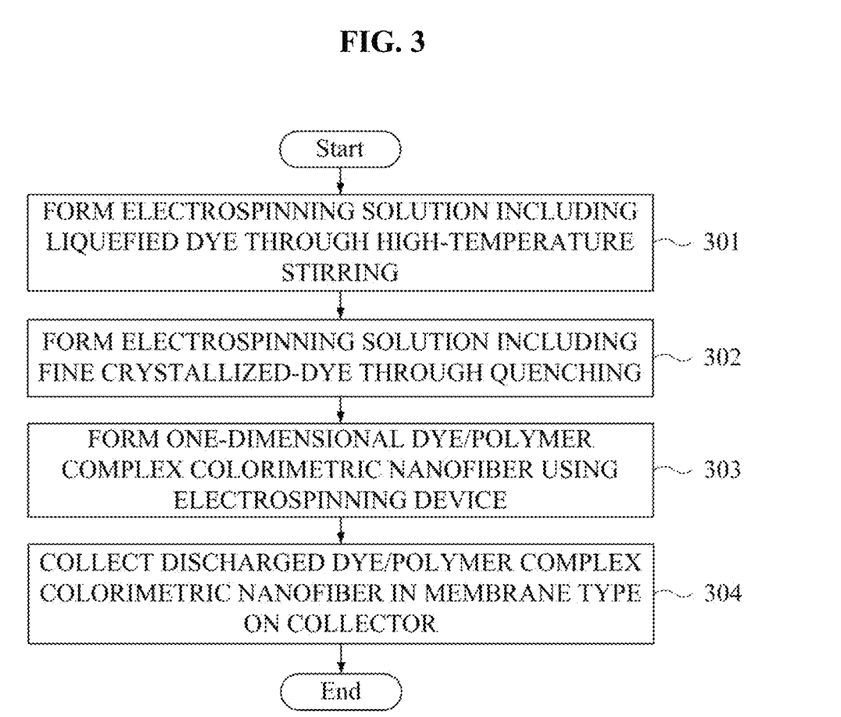
FIG. 3 is a flowchart of a manufacturing process of a dye/polymer complex nanofiber colorimetric sensor, in which nanoparticles are uniformly coupled on an inner part and a surface of the nanofiber according to an embodiment of the present disclosure.

FIG. 3 is a flowchart of a manufacturing process of a colorimetric sensor for detecting hydrogen sulfide gas using a dye/polymer complex nanofiber structure in which fine dye particles formed through high-temperature stirring and quenching are uniformly coupled to an inner part and a surface of the nanofiber using electrospinning according to an embodiment of the present invention.

In operation 301, the electrospinning solution including the liquefied dye may be manufactured through stirring at a high temperature. Herein, for obtaining the fine dye particles, the dye, the polymer, and the solvent may be stirred at a higher temperature than the melting point of the dye such that the electrospinning solution may be manufactured.

In operation 302, the electrospinning solution including the dye, which is crystallized to form microcrystals, may be manufactured. For example, the electrospinning solution formed in operation 301 may perform quenching to crystallize the dye such that the dye transforms into the microcrystals.

In operation 303, the one dimensional dye/polymer complex colorimetric nanofiber may be formed using an electrospinning equipment.

In operation 304, the discharged dye/polymer complex colorimetric nanofiber having a membrane structure may be collected on a collector.

Hereinafter, the preset disclosure will be explained through detailed examples, in detail. The examples are for illustrative purposes only, and the present disclosure is not limited thereto.

Example 1: Dye/Polymer Complex Nanofiber Synthesized Through Electrospinning of Spinning Solution Obtained by High-Temperature Stirring and Quenching of Lead(II) Acetate Trihydrate Lead(II)

For manufacture of the electrospinning solution, 0.45 g of lead(II) acetate trihydrate, 0.25 g polyacrylonitrile (PAN) having 150,000 g of molecular weight were blended into 3 ml of dimethylformamide (DMF). In order that a grain size of each dye particle was decreased to sub-μm, the dye was stirred at 90° C. i.e. more than melting point of the dye during 24 hours. A beaker, in which the electrospinning solution heated at 90° C. was contained, was rapidly dipped into a cooling water such that the quenching was performed.

Therefore, the fine dye particles were synthesized while crystal grain growth of lead(II) acetate trihydrate was controlled.

The spinning solution was connected to a nozzle. For performance of the electrospinning, 17 kV of a voltage was applied to the nozzle and a distance between the nozzle and the collector was 15 cm. In addition, a discharge rate from the nozzle was 0.3 ml/min.

Figure 4:
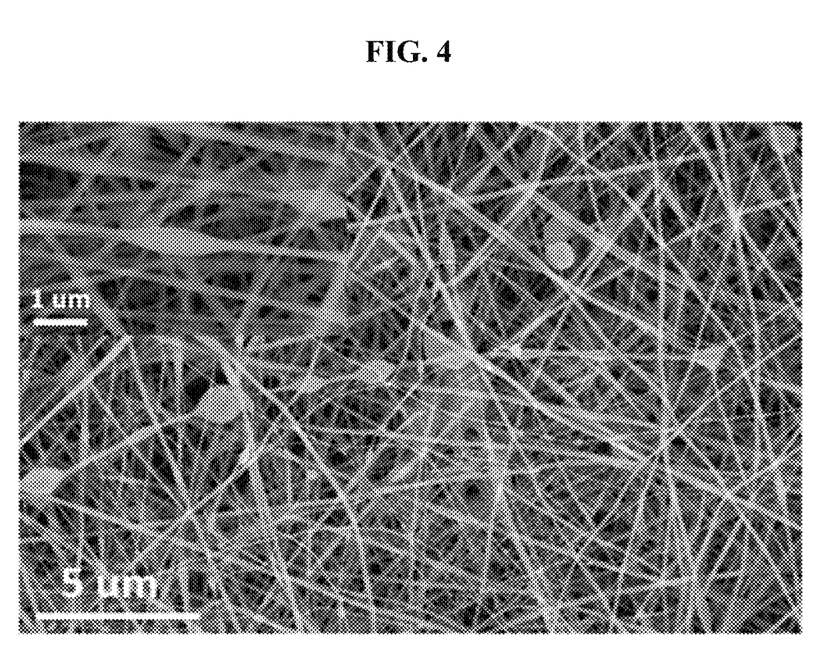
FIG. 4 is a picture of a scanning electron microscope of a dye/polymer complex nanofiber colorimetric sensor synthesized through an electrospinning process according to an example 1 of the present disclosure.

FIG. 4 is a picture of a scanning electron microscope of the dye/polymer complex nanofiber synthesized through the electrospinning process. In the electrospinning process, the polymer was elongated in a longitudinal direction such that the polymer nanofiber had the diameter of about 500 nm, while the fine dye particles remaining on the polymer and were discontinuously formed in the shape of a biconvex lens in which a ratio of a long axis to a short axis of each particle was more than 1.

Comparative Example 1. Pure Lead(II) Acetate Trihydrate Dye Particles

In comparative example 1, the pure dye particles bought on the market without the electrospinning process, unlike example 1, were used.

Figure 5:
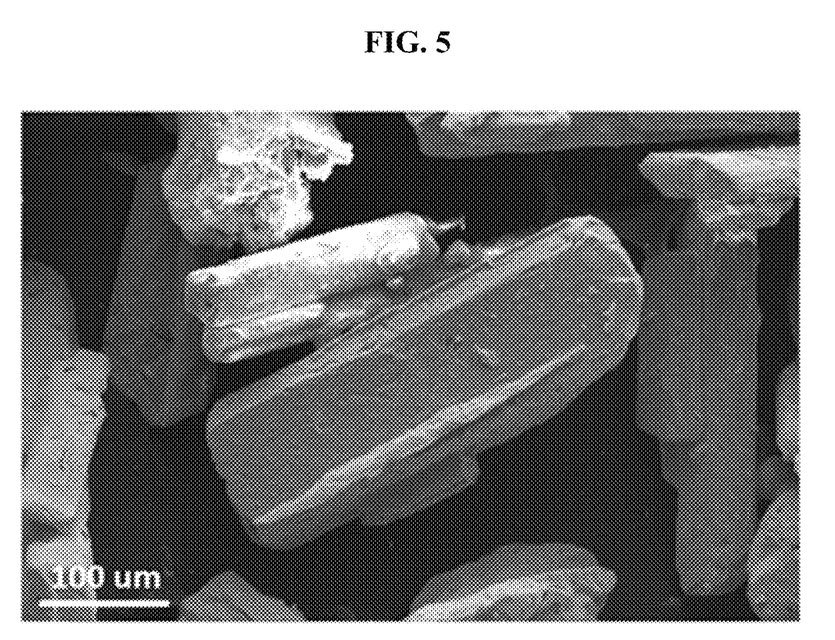
FIG. 5 is a picture of a scanning electron microscope of pure lead(II) acetate trihydrate dye particles according to comparative example 1.

FIG. 5 is a picture of a scanning electron microscope of the pure dye particles without the electrospinning process. It was shown that a size of each pure dye particle was more than 100 μm.

Comparative Example 2. Dye/Polymer Complex Nanofiber Synthesized by Electrospinning without High-Temperature Stirring and Quenching For manufacturing the electrospinning solution to be injected to the nozzle, after 0.45 g of lead(II) acetate trihydrate which was bought in market, 0.25 g polyacrylonitrile (PAN) having 150,000 g of molecular weight were blended into 3 ml of dimethylformamide (DMF), the electrospinning solution was stirred at room temperature during 24 hours. The electrospinning solution was connected to the nozzle.

For performing the electrospinning process, a voltage of 17 kV was applied to the nozzle and a distance between the nozzle and the collector was 15 cm. In addition, a discharge rate from the nozzle was 0.3 ml/min.

Figure 6:
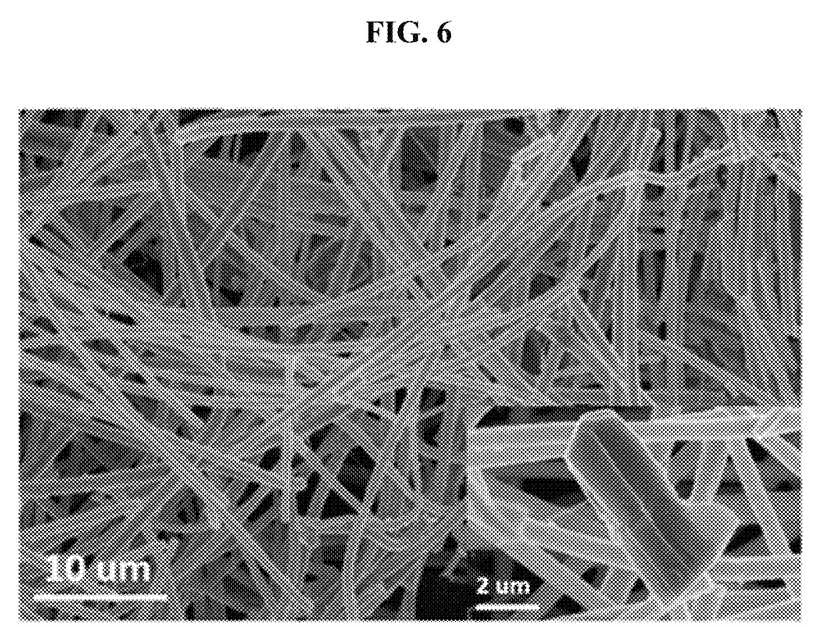
FIG. 6 is a picture of a scanning electron microscope of a dye/polymer complex nanofiber synthesized through an electrospinning process without high-temperature stirring and quenching according to comparative example 2.

FIG. 6 is a picture of a scanning electron microscope of the dye/polymer complex nanofiber formed by the electrospinning process. It was shown that a diameter distribution of the formed polymer nanofiber was about 1 μm. However, the nanofiber having the remaining dye particles could not be seen. Some bulk dye disposed in the nanofibers could be seen. This is because a great quantity of lead(II) acetate trihydrate of more than 1 μm, which was grinded by only stirring without high-temperature stirring and quenching, was hardly coupled to the surface and the inner part of the nanofiber. Accordingly, after the dye was liquefied through high-temperature stirring, crystal growth was controlled through quenching such that proper size combination of the dye particles was obtained. Therefore, the nanofiber coupled to the dye particles might be achieved.

Through below experimental example 1, when the dye/polymer nanofiber synthesized by discharging the electrospinning solution, which performed high-temperature stirring and quenching, was compared to comparative examples, it was shown that the example according to present disclosure had high detecting properties and therefore color of the dye/polymer complex nanofiber was changed although the dye/polymer complex nanofiber was exposed to a small amount of hydrogen sulfide gas.

Experimental Example 1. Colorimetric Evaluation for Detecting Hydrogen Sulfide Gas Using Dye/Polymer Complex Nanofiber Synthesized by Electrospinning Solution Performing High-Temperature Stirring and Quenching, Pure Lead(II) Acetate Trihydrate Dye Particles, and Dye/Polymer Complex Nanofiber Synthesized by Spinning without Performance High-Temperature Stirring and Quenching For evaluating colorimetric properties to hydrogen sulfide gas, materials obtained through example 1, comparative example 1, and comparative example 2 were directly exposed to hydrogen sulfide ($H_2S$) gas at normal atmospheric environment (20° C. and relative humidity of 40%) during 1 minute at a tube connected to a gas outlet as concentrations of the hydrogen sulfide gas were at 5, 1, and 0 ppm, and then the colorimetric properties were evaluated based on concentration change of the gas.

Figure 7:
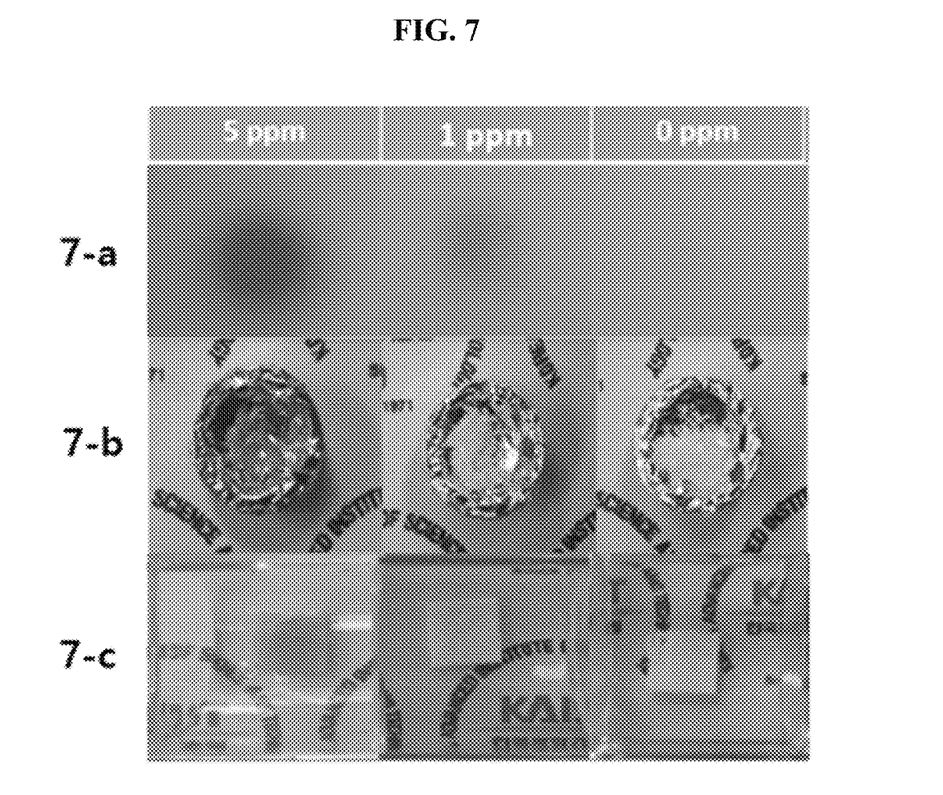
FIG. 7 shows colorimetric variation when example 1 (7-a), comparative example 1 (7-b), and comparative example 2 were directly exposed to hydrogen sulfide gas at room temperature under a dry environment without humidity during 1 minute as concentrations of the hydrogen sulfide gas were at 5, 1, and 0 ppm, respectively.

FIG. 7 shows colorimetric variation when example 1 (7-a), comparative example 1 (7-b), and comparative example 2 were directly exposed to hydrogen sulfide gas at atmospheric environment (20° C. and relative humidity of 40%) during 1 minute as concentrations of the hydrogen sulfide gas were at 5, 1, and 0 ppm.

As illustrated in FIG. 7, the dye/polymer complex colorimetric nanofiber (7-a), which performed electrospinning after high-temperature stirring and quenching, visually detected distinct color change at 1 ppm. On the contrary, it was shown that the pure lead(II) acetate trihydrate dye particles (7-b) did not display color change at 1 ppm. It was shown that the nanofiber including the dye particles (7-c) without high-temperature stirring and quenching did not display color change at 1 ppm. The dye/polymer complex colorimetric nanofiber (7-a) synthesized by electrospinning solution including the fine dye particles formed through high-temperature stirring and quenching, displayed distinct color change when being exposed to the hydrogen sulfide gas having a low concentration, in comparison with the dye particles (7-b) without the electrospinning process and the dye/polymer complex colorimetric nanofiber (7-c) without high-temperature stirring and quenching.

Figure 8:
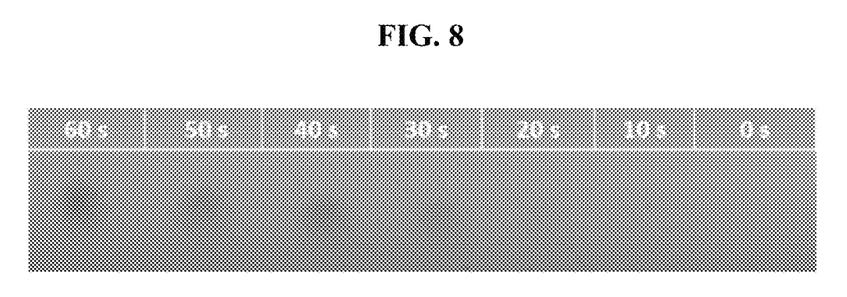
FIG. 8 shows colorimetric variation when example 1 was exposed to hydrogen sulfide gas as an exposure time was decreased to 60, 50, 40, 30, 20, 10, and 0 seconds.

FIG. 8 shows colorimetric variation when example 1 was exposed to hydrogen sulfide gas as an exposure time was decreased to 60, 50, 40, 30, 20, 10, and 0 seconds. As illustrated in FIG. 8, it was shown that distinct brown color at 1 ppm became pale as the exposure time was shortened. Color change of the nanofiber membrane exposed to sulfur gas was visually recognized up to 30 seconds. This was because lead(II) acetate trihydrate having a size of tens-of-nanometer to hundreds-of-nanometer were coupled to the surface and the inner part of the polymer nanofiber having a diameter of hundreds-of-nanometer such that gas reaction of hydrogen sulfide gas was generated at a large area. The distinct colorimetric properties was shown at a hydrogen sulfide concentration of less than 1 ppm such that hydrogen sulfide functioning as noxious environment gas and hydrogen sulfide discharged from respiration, i.e. a biomarker gas of halitosis were detected through the colorimetric sensor according to the embodiments.

As is apparent from the above description, according to the present invention, after lead(II) acetate trihydrate is stirred at a high temperature to be liquefied and the fine dye particles in a liquid state is uniformly dispersed in the solution, quenching is performed such that the lead(II) acetate trihydrate dye particles having a size of tens-of-nanometer and hundreds-of-nanometer, in particularly, having a size range of 20 to 500 nm are obtained. The dispersed solution performs the electrospinning process such that the complex nanofiber detecting material, in which the fine dye particles uniformly remains in the inner and outer parts of the one-dimensional nanofiber, is synthesized. Thereby, the polymer nanofiber sensor for detecting hydrogen sulfide gas, which is coupled to the fine lead(II) acetate particles able to selectively react with the small amount of hydrogen sulfide, may be provided.

The dye/polymer complex nanofiber has the surface area and porosity which are higher than those of the dye material of the existing test paper for detecting hydrogen sulfide. Therefore, although the dye/polymer complex nanofiber is exposed to hydrogen sulfide having a concentration of less than 1 ppm, color change is visible within tens-of-second such that the dye/polymer complex nanofiber may be used as the colorimetric sensor capable of diagnosing halitosis and monitoring noxious hydrogen sulfide gas with a high sensitivity and at high speed.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A polymer nanofiber sensor for hydrogen sulfide gas indication comprising:
   polymer nanofibers; and
   a dye material coupled to the polymer nanofibers,
   wherein dye particles of the dye material is coupled to an inner part and a surface of the polymer nanofibers, the dye particles being formed by a melting process in which the dye material is stirred at a high temperature of more than melting point of the dye material and a quenching process in which the melted dye material is changed to the dye particles, and
   a color of the dye material is changed through a reaction to a specific gas, the specific gas being hydrogen sulfide gas, wherein a concentration of said hydrogen sulfide gas is 1.0 ppm or less.

2. The polymer nanofiber sensor of claim 1, wherein the dye material includes lead(II) acetate whose color is changed during a reaction to hydrogen sulfide (H2S) such that lead sulfide (PbS) is formed.

3. The polymer nanofiber sensor of claim 1, wherein the dye material includes lead(II) acetate trihydrate (Pb($CH_3COO$)$_2$.3H2O, 75° C. of melting point) having relatively low melting point, which is selected from lead(II) acetate anhydrous (Pb($CH_3COO$)$_2$, 280° C. of melting point) and lead(II) acetate trihydrate.

4. The polymer nanofiber sensor of claim 1, wherein the dye material is elongated in a longitudinal direction during an electrospinning process of an electrospinning solution including the polymer and the dye material, such that the dye material is formed in the shape of a biconvex lens in which a ratio of a long axis to a short axis is more than 1.

5. The polymer nanofiber sensor of claim 1, wherein, when the dye material in the shape of a biconvex lens in which a ratio of a long axis to a short axis is more than 1, a diameter of the short axis includes a range of 10 to 500 nm and a diameter of the long axis includes a range of 100 nm to 5 µm such that the dye material having a particle shape is coupled to the polymer nanofiber.

6. The polymer nanofiber sensor of claim 1, wherein the dye material includes lead(II) acetate trihydrate, and
wherein the polymer and lead(II) acetate trihydrate are melted at a high temperature of more than melting point (75° C.) of lead(II) acetate trihydrate to form an electrospinning solution, the electrospinning solution is dipped in cooling water, and the electrospinning solution performs an electrospinning process such that a dye-polymer complex nanofiber is formed in which the dye material is intensively coupled to the polymer nanofiber without desorption.

7. The polymer nanofiber sensor of claim 1, wherein the polymer nanofiber has a diameter range of 50 nm to 2 µm.

8. The polymer nanofiber sensor of claim 1, wherein the dye material has a weight rate range of 0.5 to 90 wt % with respect to polymer included in the polymer nanofiber.

* * * * *